US011096613B2

(12) United States Patent
Ghannam et al.

(10) Patent No.: US 11,096,613 B2
(45) Date of Patent: Aug. 24, 2021

(54) SYSTEMS AND METHODS FOR REDUCING ANXIETY IN AN OCCUPANT OF A VEHICLE

(71) Applicant: Ford Global Technologies, LLC, Dearborn, MI (US)

(72) Inventors: Mahmoud Yousef Ghannam, Canton, MI (US); Aed M. Dudar, Canton, MI (US); Brian Bennie, Sterling Heights, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 0 days.

(21) Appl. No.: 16/561,672

(22) Filed: Sep. 5, 2019

(65) Prior Publication Data

US 2021/0068737 A1    Mar. 11, 2021

(51) Int. Cl.
  *B60N 2/02*      (2006.01)
  *A61B 5/18*      (2006.01)
  *A61M 21/02*     (2006.01)
  *B60W 40/09*     (2012.01)
  *B60W 40/08*     (2012.01)

(52) U.S. Cl.
  CPC ............... *A61B 5/18* (2013.01); *A61M 21/02* (2013.01); *B60W 40/09* (2013.01); *B60W 2040/0872* (2013.01); *B60W 2540/22* (2013.01)

(58) Field of Classification Search
  CPC ......... A61M 21/02; A61B 5/18; B60W 40/09; B60W 2040/0872; B60W 2540/22
  See application file for complete search history.

(56) References Cited

U.S. PATENT DOCUMENTS

| | | | | |
|---|---|---|---|---|
| 10,150,351 | B2 * | 12/2018 | Lin | B60H 3/0035 |
| 2015/0053066 | A1 * | 2/2015 | Hampiholi | B60K 37/06 84/602 |
| 2016/0089954 | A1 * | 3/2016 | Rojas Villanueva | B60H 1/00742 701/36 |
| 2016/0264021 | A1 * | 9/2016 | Gillett | B60K 37/06 |
| 2017/0028876 | A1 * | 2/2017 | Yamada | B60N 2/06 |
| 2018/0225551 | A1 * | 8/2018 | Lin | B60H 3/0035 |
| 2019/0126914 | A1 * | 5/2019 | Nojoumian | G05D 1/0055 |
| 2019/0232974 | A1 * | 8/2019 | Reiley | B60W 60/0013 |
| 2020/0134672 | A1 * | 4/2020 | el Kaliouby | G06K 9/00845 |

* cited by examiner

*Primary Examiner* — Munear T Akki
(74) *Attorney, Agent, or Firm* — Frank Lollo; Eversheds Sutherland (US) LLP (57) ABSTRACT

Exemplary embodiments described in this disclosure are generally directed to systems and methods for reducing anxiety in an occupant of a vehicle. In one exemplary method, a computer that is provided in a vehicle receives from a source such as a server computer, information that is used to determine a behavioral profile of an occupant of the vehicle. The computer utilizes the behavioral profile to identify a behavior characteristic of the occupant. The behavior characteristic is matched by the computer to one of various behavior categories such as an amaxophobia sufferer category or a controlling personality category. The computer then executes one or more operations in the vehicle based on the behavior category to which the occupant belongs. If the occupant belongs to the amaxophobia sufferer category, the computer may, for example, play an audio track, display a video clip, and/or change a driving characteristic of the vehicle.

19 Claims, 4 Drawing Sheets

FIG. 5

SYSTEMS AND METHODS FOR REDUCING ANXIETY IN AN OCCUPANT OF A VEHICLE

FIELD OF THE DISCLOSURE

This disclosure generally relates to vehicles, and more particularly relates to systems and methods for reducing anxiety in an occupant of a vehicle.

BACKGROUND

Most people encounter some level of anxiety when driving a vehicle. For example, a driver of a vehicle may have various levels of anxiety when performing actions such as waiting for a red light to turn green, changing lanes on an expressway, or looking out for a traffic policeman while driving over the speed limit. Such levels of anxiety may be deemed normal in most cases. In some cases, though, the driver may have an abnormally high level of anxiety that could potentially lead to dangerous situations, such as rear-ending of the vehicle due to the driver braking at the wrong times, or driving dangerously below the speed limit. It is therefore desirable to provide solutions that minimize or eliminate such abnormally high levels of anxiety.

In the case of passengers of a vehicle, the anxiety levels may be higher than that of a driver, primarily because a passenger does not have control of the vehicle. Some passengers, such as a child, for example, may trust the driving skills of a parent and may consequently be more relaxed than if the parent was the passenger and the child was driving the vehicle. The problem is particularly exacerbated when the passenger has a controlling type of personality. Utterances from the driver such as "Calm down, will you" "Don't worry, I'm a good driver," or "stop nagging me" prove particularly ineffective in reducing the anxiety of a passenger. It is therefore desirable to provide more effective solutions for mitigating anxiety in a passenger of a vehicle as well.

In some cases, an occupant of a vehicle (either a driver or a passenger), may suffer from an abnormal fear of riding in a vehicle. This condition, which is generally referred to as amaxophobia, may be caused by various factors such as due to a traumatic event in the past or a genetic predisposition to amaxophobia. It is desirable to provide solutions that minimize or eliminate anxiety in persons suffering from amaxophobia when these persons are occupants of a vehicle.

BRIEF DESCRIPTION OF THE DRAWINGS

A detailed description is set forth below with reference to the accompanying drawings. The use of the same reference numerals may indicate similar or identical items. Various embodiments may utilize elements and/or components other than those illustrated in the drawings, and some elements and/or components may not be present in various embodiments. Elements and/or components in the figures are not necessarily drawn to scale. Throughout this disclosure, depending on the context, singular and plural terminology may be used interchangeably.

DETAILED DESCRIPTION

Overview

In terms of a general overview, certain embodiments described in this disclosure are generally directed to systems and methods for reducing anxiety in an occupant of a vehicle. In one exemplary method, a computer that is provided in a vehicle receives from a source such as a server computer or a cloud storage component, information that is used to determine a behavioral profile of an occupant of the vehicle. The computer utilizes the behavioral profile to determine a behavior characteristic of the occupant. The behavior characteristic is matched by the computer to one of various behavior categories such as, for example, an amaxophobia sufferer category or a controlling personality category. The computer then executes one or more operations in the vehicle based on the behavior category to which the occupant belongs. If the occupant belongs to the amaxophobia sufferer category, the computer may, for example, play an audio track, display a video clip, and/or change a driving characteristic of the vehicle.

Illustrative Embodiments

The disclosure will be described more fully hereinafter with reference to the accompanying drawings, in which exemplary embodiments of the disclosure are shown. This disclosure may, however, be embodied in many different forms and should not be construed as limited to the exemplary embodiments set forth herein. It will be apparent to persons skilled in the relevant art that various changes in form and detail can be made to various embodiments without departing from the spirit and scope of the present disclosure. Thus, the breadth and scope of the present disclosure should not be limited by any of the above-described exemplary embodiments but should be defined only in accordance with the following claims and their equivalents. The description below has been presented for the purposes of illustration and is not intended to be exhaustive or to be limited to the precise form disclosed. It should be understood that alternate implementations may be used in any combination desired to form additional hybrid implementations of the present disclosure. For example, any of the functionality described with respect to a particular device or component may be performed by another device or component. Furthermore, while specific device characteristics have been described, embodiments of the disclosure may relate to numerous other device characteristics. Further, although embodiments have been described in language specific to structural features and/or methodological acts, it is to be understood that the disclosure is not necessarily limited to the specific features or acts described. Rather, the specific features and acts are disclosed as illustrative forms of implementing the embodiments.

Certain words and phrases are used herein solely for convenience and such words and terms should be interpreted as referring to various objects and actions that are generally understood in various forms and equivalencies by persons of ordinary skill in the art. For example, the word "vehicle" as used in this disclosure can pertain to any one of various types of vehicles such as cars, vans, sports utility vehicles, trucks, electric vehicles, gasoline vehicles, hybrid vehicles, and autonomous vehicles. The word "anxiety" as used in this disclosure can represent any of a wide range of emotions that are generally understood to be undesirable, such as, for example, stress, anger, annoyance, irritation, fear, and panic. The label "autonomous vehicle" as used herein encompasses various other equivalent labels such as "self-driving vehicle," "robotic vehicle," and "driverless vehicle." Furthermore, it should be understood that the word "example" as used herein is intended to be non-exclusionary and non-limiting in nature. More particularly, the word "exemplary" as used herein indicates one among several examples, and it should be understood that no undue emphasis or preference is being directed to the particular example being described.

Figure 1:
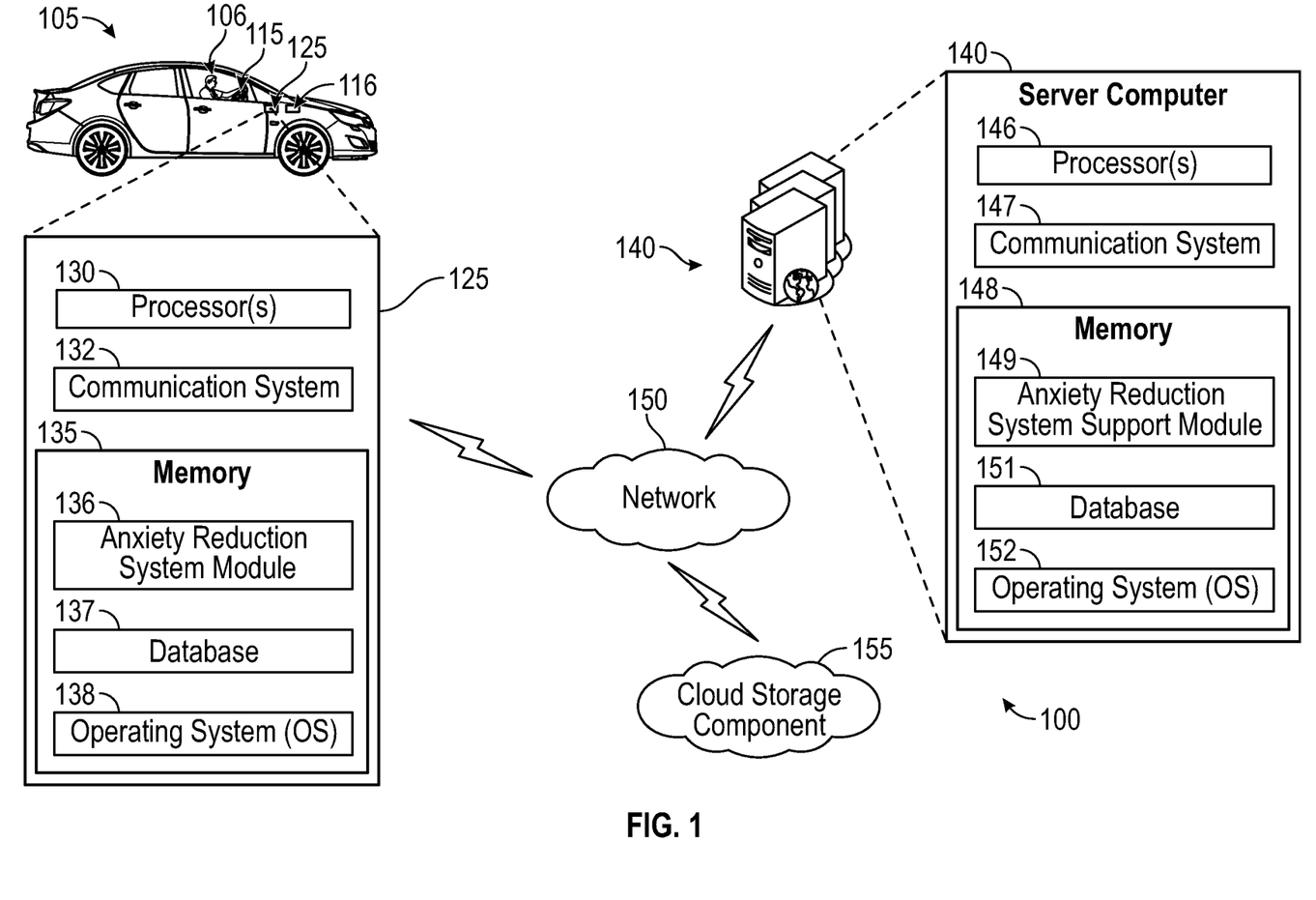
FIG. 1 shows a system for reducing anxiety in an occupant of a vehicle in accordance with an exemplary embodiment of the disclosure.

FIG. 1 shows a system 100 for reducing anxiety in an occupant 106 of a vehicle 105 in accordance with an exemplary embodiment of the disclosure. In a first exemplary implementation of this embodiment, the vehicle 105 is an autonomous vehicle and the occupant 106 is a passenger in the autonomous vehicle. In a second exemplary implementation of this embodiment, the vehicle 105 is operated by a driver and the occupant 106 can either be the driver or a passenger in the vehicle 105.

The vehicle 105 may include one or more computers such as a vehicle computer 116 and a computer 125. The vehicle computer 116 may perform various functions associated with operating the vehicle 105 such as, for example, controlling engine operations (fuel injection, speed control, emissions control, braking, etc.), managing climate controls (air conditioning, heating etc.), activating airbags, and issuing warnings (check engine light, bulb failure, low tire pressure, vehicle in blind spot, etc.). In some cases, the vehicle computer 116 may include more than one computer such as, for example, a first computer that controls engine operations and a second computer that operates an infotainment system 115.

The computer 125 is configured to execute various actions in accordance with the disclosure. In some implementations, the computer 125 may be a standalone computer that is provided in the vehicle 105. In some other implementations, some or all of the components of the computer 125 may be shared with the vehicle computer 116. The computer 125 may be communicatively coupled to various components in the vehicle 105, such as, for example, the vehicle computer 116, the infotainment system 115, and various sensors, motors and/or actuators. The computer 125 may also be communicatively coupled via a network 150 to various components outside the vehicle 105, such as for example, a server computer 140 and a cloud storage component 155.

The network 150 may include any one, or a combination of networks, such as a local area network (LAN), a wide area network (WAN), a telephone network, a cellular network, a cable network, a wireless network, and/or private/public networks such as the Internet. For example, the network 150 may support communication technologies such as TCP/IP, Bluetooth, cellular, near-field communication (NFC), Wi-Fi, Wi-Fi direct, machine-to-machine communication, and/or man-to-machine communication. At least one portion of the network 150 can include a wireless communication link that allows the computer 125 in the vehicle 105 to wirelessly communicate with the server computer 140.

In some applications, the server computer 140 may cooperate with the computer 125 to carry out some operations associated with reducing anxiety in the occupant 106 of the vehicle 105 in accordance with the disclosure. In one such exemplary application, the server computer 140 may be configured to operate as a master computing element that executes various processing operations in accordance with the disclosure and provides instructions and/or commands to the computer 125 to carry out certain actions based on the processing. The computer 125 operates as a slave computing element in this application. In another exemplary application, the computer 125 may execute various operations in accordance with the disclosure and use the server computer 140 as a data repository. The computer 125 may also use the cloud storage component 155 to store information, in addition to, or in place of, the server computer 140.

The computer 125 may include a processor 130, a communication system 132, and a memory 135. The communication system 132 can include a transceiver that allows the computer 125 to communicate with various components such as the vehicle computer 116 and the infotainment system 115. The communications between the computer 125 and the various components in the vehicle 105 may be carried out over a bus (not shown). The bus can be implemented using one or more of various wired and/or wireless technologies. For example, the bus can be a vehicle bus that uses a controller area network (CAN) bus protocol, a Media Oriented Systems Transport (MOST) bus protocol, and/or a CAN flexible data (CAN-FD) bus protocol.

Some or all portions of the bus may also be implemented using wireless technologies such as Bluetooth®, Zigbee®, or near-field-communications (NFC), cellular, Wi-Fi, Wi-Fi direct, machine-to-machine communication, and/or man-to-machine communication to communicate with devices such as a smartphone carried by the occupant 106 of the vehicle 105. At least some of the information generated by the computer 125 in accordance with the disclosure may be wirelessly transmitted by the communication system 132 for display on the smartphone and/or on the infotainment system 115.

The memory 135, which is one example of a non-transitory computer-readable medium, may be used to store an operating system (OS) 138 and one or more code modules such as an anxiety reduction system module 136. The code modules can be provided in the form of computer-executable instructions that are executed by the processor 130 for performing various operations in accordance with the disclosure. The memory 135 may also include a database 137 that may be used to store information pertaining to the occupant 106 and other occupants of other vehicles. The information may be used by the processor 130 to determine a behavior characteristic of the occupant 106, for example. In one case, the information may indicate to the processor 130 that the occupant 106 is prone to suffering from amaxophobia, or that the occupant 106 has a controlling personality.

The vehicle 105 may also include an infotainment system 115, which can be an integrated unit that includes various components such as a radio, a CD player, a video player, and a navigation system. In an exemplary implementation, the infotainment system 115 may include a display having a graphical user interface (GUI) for use by the occupant 106 of the vehicle 105. The occupant 106 may use the GUI to interact with the computer 125 and/or to operate the components of the infotainment system 115 such as to listen to music on the radio or CD player.

The server computer 140 may include a processor 146, a communication system 147, and a memory 148. The communication system 147 can include a transceiver that allows the server computer 140 to communicate with the computer 125 in the vehicle 105 via the network 150. The memory 148, which is another example of a non-transitory computer-readable medium, may be used to store an operating system (OS) 152 and one or more code modules such as an anxiety reduction system support module 149. The code modules can be provided in the form of computer-executable instructions that are executed by the processor 140 for performing various operations in accordance with the disclosure.

The anxiety reduction system support module 149 may be executed by the processor 146 to perform functions that are substantially similar to, or complementary to, at least some functions carried out by the processor 130 via execution of the anxiety reduction system module 136 in the computer 125. The database 151 may be used to store information pertaining to the occupant 106 and other occupants of other vehicles. The information, which may be similar to, or different than, the information contained in the database 137, may be used by the processor 146 and/or provided to the computer 125 upon request.

Figure 2:
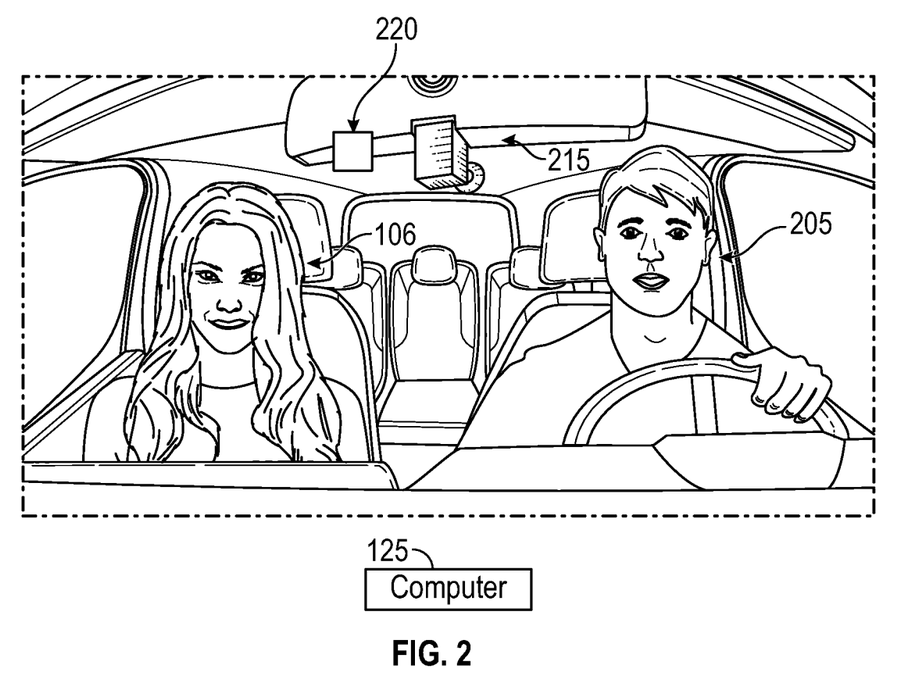
FIG. 2 shows an exemplary illustration of an occupant of a vehicle suffering from anxiety.

FIG. 2 shows an exemplary illustration of the occupant 106 of the vehicle 105 when suffering from anxiety. In an example implementation, the vehicle 105 can include an imaging system 215 that is arranged to capture images of some or all of the occupants of the vehicle 105. In this exemplary illustration, the imaging system 215, which can be a digital camera or a video camera, captures an image and/or a video clip of an interior portion of the vehicle 105 and propagates the image and/or video clip to the computer 125. The computer 125 processes the image and/or video clip to determine a behavior characteristic/category of the occupant 106 and/or the occupant 205. For example, the computer 125 may assess some facial features of the occupant 106 and make a determination that the occupant 106 is suffering from anxiety. Some exemplary features may include a furrowed brow, pursed lips, and narrowed eyes. The anxiety may be caused due to various factors such as, for example, a manner in which the vehicle is being operated (high speed, heavy braking, etc.) or due to the occupant 106 suffering from amaxophobia.

In another example implementation, the vehicle 105 can include various sensors such as, for example, a pressure sensor located in a door handle of the vehicle 105 and/or a pressure sensor located in a seat in which the occupant is seated. The pressure sensors may provide sensor readings to the computer 125, and the computer 125 can evaluate the sensor readings to determine a behavior characteristic of the occupant 106. For example, the computer 125 may determine from a sensor reading provided by the pressure sensor in the door handle that the occupant 106 is gripping the door handle with excessive force. Such an action may be indicative of a high level of anxiety. Similarly, the computer 125 may determine from a sensor reading provided by the pressure sensor in the seat that the occupant 106 is fidgety. Such an action may be indicative of a high level of anxiety.

In yet another example implementation, the vehicle 105 can include various audio transducers such as, for example, a microphone 220 located in a visor in the vehicle 105. The microphone 220 may provide to the computer 125, a digitized version of various utterances made by the occupant 106. The computer 125 may evaluate the utterances to detect various key words that may be indicative of anxiety, such as, for example, "slow down," "watch out," "brake! brake!!" and "accident."

The vehicle 105 can also include various biosensors such as, for example, a heart rate monitoring system or a blood pressure monitoring system. The bio sensors may be embedded, for example, in a door handle of the vehicle 105. Biometric measurements carried out by such biosensors upon the occupant 106 may be provided to the computer 125 for determining a behavior characteristic of the occupant 106. Abnormally high readings may indicate that the occupant 106 is suffering from anxiety.

Some or all of the various components and procedures described above with reference to the occupant 106 may be used to determine a behavior characteristic of the occupant 205 as well. The determination made by the computer 125 of the behavior characteristic of the occupant 205 may be similar to or different than that of the occupant 106. For example, an evaluation of information provided to the computer 125, such as an image captured by the imaging system 215, various utterances made by the occupant 205, sensor readings associated with the occupant 205, and/or biometric measurements of the occupant 205 may provide to the computer 125, an indication that the occupant 205 has a controlling personality. Key words or phrases uttered by the occupant 205 may include, for example, "calm down," "relax, will you?" and "you are such a bad driver."

Some of the descriptions provided above with reference to the computer 125 being used to determine that the occupant 106 suffers from amaxophobia (amaxophobia sufferer category) and that the occupant 205 has a controlling personality (controlling personality), may be equally relevant to the computer 125 being used to determine various other types of behavior categories. A few examples of other behavior categories may include a complaining personality category, a passive personality category, a submissive personality category, and a judgmental personality category.

Figure 3:
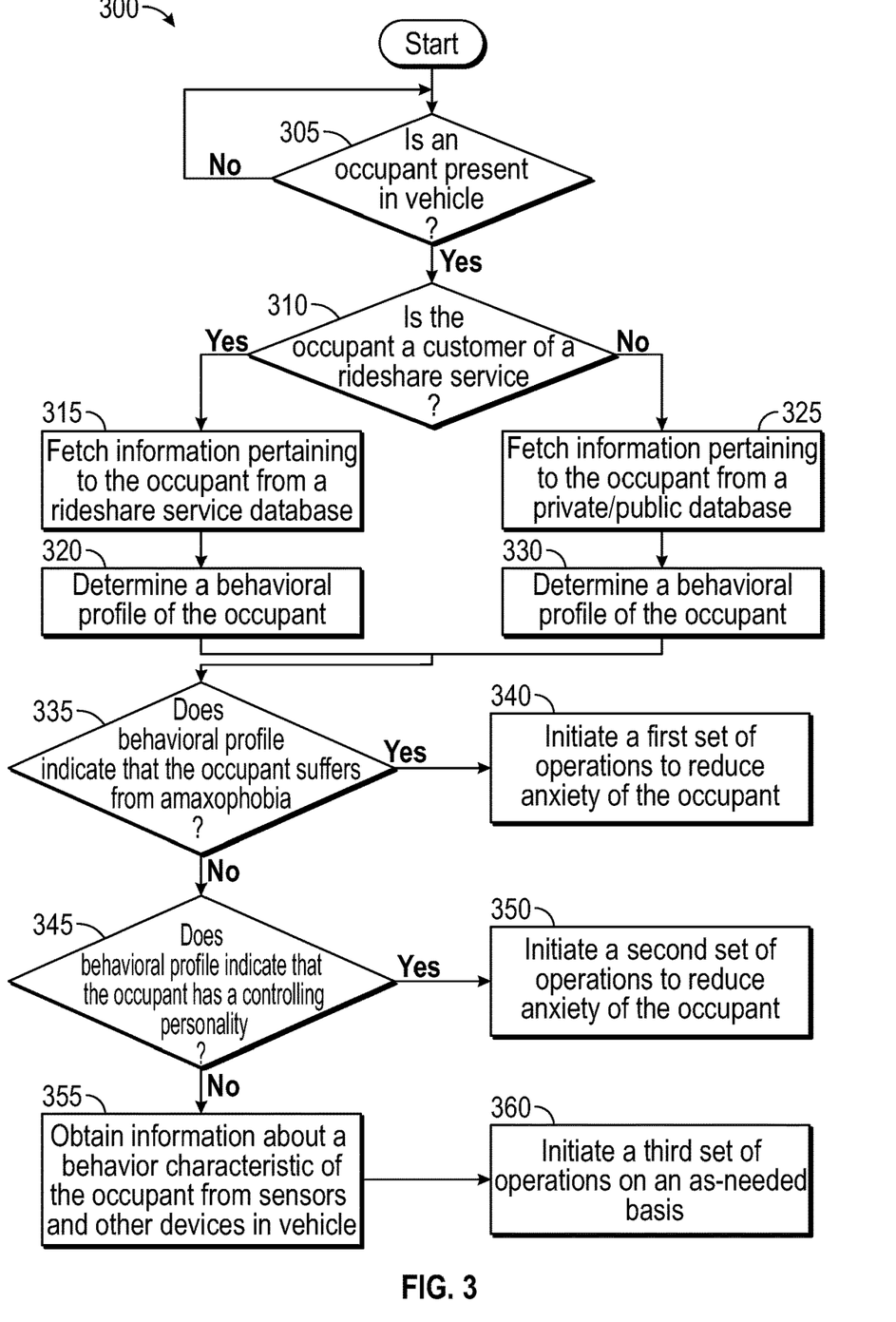
FIG. 3 illustrates a flowchart of an exemplary method to identify and reduce anxiety in an occupant of a vehicle in accordance with an embodiment of the disclosure.

FIG. 3 shows an exemplary flowchart 300 of a method to reduce anxiety in an occupant of a vehicle in accordance with the disclosure. The flowchart 300 illustrates a sequence of operations that can be implemented in hardware, software, or a combination thereof. In the context of software, the operations represent computer-executable instructions stored on one or more non-transitory computer-readable media such as the memory 135 or the memory 148, that, when executed by one or more processors such as the processor 130 or the processor 146 respectively, perform the recited operations. Generally, computer-executable instructions include routines, programs, objects, components, data structures, and the like that perform particular functions or implement particular abstract data types. The order in which the operations are described is not intended to be construed as a limitation, and any number of the described operations may be carried out in a different order, omitted, combined in any order, and/or carried out in parallel. Some or all of the operations described in the flowchart 300 may be carried out by using an application such as the anxiety reduction system module 136 in the memory 135 of the computer 125 and/or the anxiety reduction system support module 149 in the memory 148 of the server computer 140. Some of the aspects of the flowchart 300 are described below using the system 100 shown in FIG. 1 and the occupants shown in FIG. 2. However, it should be understood that the description is equally applicable to various other embodiments in accordance with the disclosure.

At block 305, the computer 125 may make a determination whether there is an occupant present in the vehicle 105. This operation may be carried out by using devices such as the imaging system 215, the microphone 220, and/or the various sensors in the vehicle 105. The computer 125 may process data provided by one or more of the devices and identify, for example, the presence of the occupant 106 in the vehicle 105. It must be understood that the description provided below with respect to the occupant 106 is equally applicable to other occupants of the vehicle 105, such as the occupant 205 shown in FIG. 2.

At block 310, the computer 125 may make a determination whether the occupant 106 is a customer of a rideshare service such as Uber® or Lyft®. This determination, which is made automatically by the computer 125 without human intervention, may be particularly applicable when the vehicle 105 is an autonomous vehicle operated by an entity such as a rideshare service, a taxi service, a limousine service, or a shuttle service.

If the occupant 106 is a customer of a rideshare service, at block 315, the computer 125 may use the communication system 132 to communicate with the server computer 140 for fetching a first type of information that pertains to the occupant 106. In one exemplary implementation, the communication system 132 may communicate with the server computer 140 using a vehicle-to-everything (V2X) communication format, and the server computer 140 may be used to store and to operate upon information that is proprietary to the rideshare service. The first type of information, which may be stored in the database 151 of the server computer 140 and/or fetched by the server computer 140 from the cloud storage component 155, may include data that the occupant 106 has offered voluntarily to the rideshare service (such as personal information, financial information, and feedback pertaining to previous rides). The first type of information pertaining to the occupant 106 may also be data obtained by the rideshare service from sources such as financial institutions and credit bureaus, and/or a personal profile that the rideshare service may have created of the occupant 106.

At block 320, the computer 125 may identify a behavioral profile of the occupant 106 by processing the first type of information received from the server computer 140. For example, the computer 125 may identify the behavioral profile of the occupant 106 by processing the feedback provided by the occupant 106 after undertaking previous rides in various automobiles of the rideshare service. The feedback may indicate that the occupant 106 has an anxious behavioral characteristic, a complimentary behavioral characteristic, a complaining behavioral characteristic, or an obsessive behavioral characteristic, for example.

If the occupant 106 is not a customer of a rideshare, at block 325, the computer 125 may use the communication system 132 to communicate with the server computer 140 for fetching a second type of information that pertains to the occupant 106. In an exemplary implementation, the second type of information, which may be stored in the database 151 of the server computer 140 and/or in the cloud storage component 155, may be accessible to the public and/or may be accessible to a private entity such as a company or a corporation. The communication between the computer 125 and the server computer 140 may be carried out by using a vehicle-to-everything (V2X) communication format. The second type of information that is fetched by the computer 125 from the server computer 140, may include information about the occupant 106 that exists in the public domain such as, for example, government records, police records, hospital records, social media content, and media reports such as newspaper articles pertaining to the occupant 106.

At block 330, the computer 125 may process the second type of information received from the server computer 140 to identify a behavioral profile of the occupant 106. For example, the computer 125 may identify the behavioral profile of the occupant 106 by processing the hospital records of the occupant 106, which may indicate that the occupant 106 has suffered a traumatic incident in the past, particularly a traffic related incident or a traffic accident.

At block 335, the computer 125 may make a determination whether the behavioral profile of the occupant 106 indicates that the occupant 106 suffers from amaxophobia. If the behavioral profile of the occupant 106 indicates that the occupant 106 suffers from amaxophobia, at block 340, the computer 125 may initiate a first set of operations to reduce anxiety associated with an individual suffering from amaxophobia. Some exemplary operations of this nature are described below.

If the behavioral profile of the occupant 106 indicates that the occupant 106 does not suffer from amaxophobia, at block 345, the computer 125 may make a determination whether the behavioral profile of the occupant 106 indicates that the occupant 106 has a controlling personality. If the behavioral profile of the occupant 106 indicates that the occupant 106 has a controlling personality, at block 350, the computer 125 may initiate a second set of operations to reduce anxiety associated with an individual having a controlling personality. Some exemplary operations of this nature are described below.

If the behavioral profile of the occupant 106 indicates that the occupant 106 does not have a controlling personality, at block 355, the computer 125 may obtain data via various devices in the vehicle 105 such as the imaging system 215, the microphone 220, and/or the various sensors in the vehicle 105. The computer 125 may process this data to determine a behavior characteristic of the occupant 106. More particularly, the computer 125 may match the behavior characteristic of the occupant 106 to a specific behavior category in a set of behavior categories. The set of behavior categories that are used for determining the match may include, for example, a complaining personality category, a passive personality category, a submissive personality category, and a judgmental personality category. Based on the specific behavior category determined by the computer 125, at block 360, the computer 125 may carry out a third set of operations on an as-needed basis to reduce anxiety in the occupant 106.

A few examples of the first set of operations carried out by the computer 125 (block 340) upon determining that the occupant 106 belongs to the amaxophobia sufferer category, may involve the computer 125 cooperating with the vehicle computer 116 to play soft music on the infotainment system 115, display pleasant images on the infotainment system 115, play certain types of audio clips on the infotainment system 115 (such as describing safety features incorporated into the vehicle 105), offer games on the infotainment system 115 (a fidget spinner game, for example), activate a massaging function in a seat occupied by the occupant 106, modify a setting of a lighting system in the vehicle 105, modify a driving characteristic of the vehicle 105, and/or modify a component of the vehicle 105 such as repositioning a seat or increasing a level of tinting in a window.

A few examples of the second set of operations carried out by the computer 125 (block 350) upon determining that the occupant 106 belongs to the controlling personality category may involve the computer 125 cooperating with the vehicle computer 116 to offer the occupant 106 a level of control upon certain components of the vehicle 105, such as allowing the occupant 106 to carry out various adjustments to a seat or a window of the vehicle 105. The computer 125 may also offer the occupant 106 a choice to modify a driving characteristic of the vehicle 105.

A few examples of the third set of operations carried out by the computer 125 (block 360) upon determining that the occupant 106 belongs to one of a complaining personality category, a passive personality category, a submissive personality category, and a judgmental personality category may be based on a majority vote procedure. In one exemplary majority vote procedure, the computer 125 may poll the occupants of the vehicle 105 prior to carrying out an action in the vehicle 105. For example, the computer 125 may use the infotainment system 115 to issue audible instructions for voting and the microphone 220 to obtain responses from the occupants of the vehicle 105 with respect to making a determination as to, for example, what type of music to play on the infotainment system 115, a temperature setting of a climate control system in the vehicle 105, or a lighting level in the vehicle 105. An occupant having a passive personality category or a submissive personality category may have no objections to such a majority vote procedure, and the occupant with either the complaining personality category or the judgmental personality category may be compelled to follow democratic norms and allow the majority will to prevail.

Figure 4:
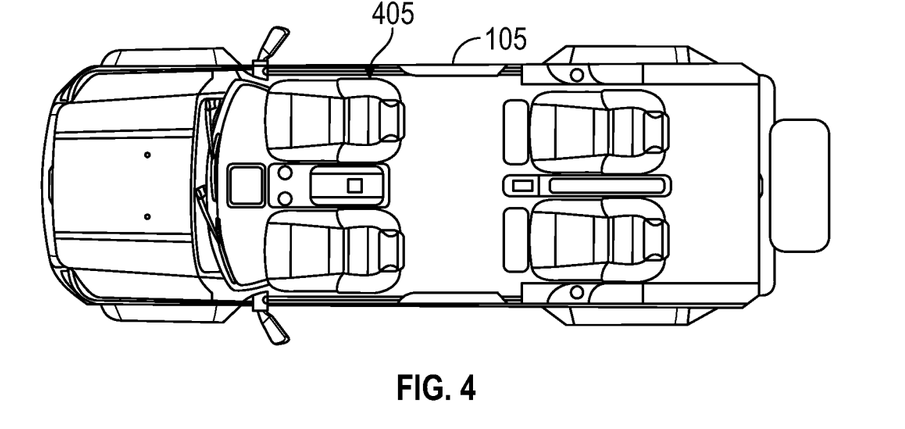
FIG. 4 shows a first exemplary seating configuration in a vehicle.

FIG. 4 shows a first exemplary seating configuration in the vehicle 105. In this seating configuration, the occupant 106 may be seated in a seat 405 that faces a windshield of the vehicle 105. In an exemplary operation, the computer 125 may execute the flowchart described above and determine that the occupant 106 suffers from amaxophobia. Having an unobstructed field of view of various objects outside the vehicle 105, such as a vehicle overtaking the vehicle 105 at high speed, a vehicle braking abruptly in front of the vehicle 105, or buildings rushing by as a result of the vehicle 105 traveling at high speed, may exacerbate the feeling of amaxophobia in the occupant 106. In this scenario, the computer 125 may use the imaging system 215, the microphone 220, and/or the various sensors in the vehicle 105 to determine that an anxiety level of the occupant 106 is increasing. The computer 125 may then carry out certain operations to reduce the anxiety level of the occupant 106. One such operation involves modifying an orientation of the seat 405 so as to avoid providing a view out of the windshield of the vehicle 105.

Figure 5:
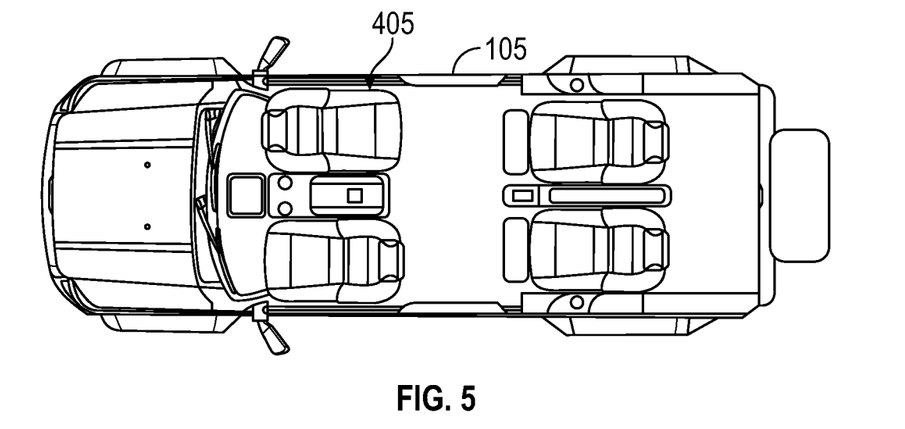
FIG. 5 shows a modification of the first exemplary seating configuration that may be carried out in order to reduce anxiety in an occupant of a vehicle.

FIG. 5 shows a modification of the first exemplary seating configuration that may be carried out to avoid providing the occupant 106, a view out of the windshield of the vehicle 105. The computer 125 may provide one or more control signals to a motor (not shown) located underneath the seat 405 so as to rotate the seat 405. The occupant 106 may now be seated facing other occupants of the vehicle 105 rather than looking forwards out of the vehicle 105. Interacting with these other occupants, such as chatting with the other occupants, may reduce the anxiety in the occupant 106. Additional actions may also be taken by the computer 125 to further reduce anxiety such as, for example, increasing a level of tinting of the windows of the vehicle 105.

In the above disclosure, reference has been made to the accompanying drawings, which form a part hereof, which illustrate specific implementations in which the present disclosure may be practiced. It is understood that other implementations may be utilized, and structural changes may be made without departing from the scope of the present disclosure. References in the specification to "one embodiment," "an embodiment," "an example embodiment," "an exemplary embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, one skilled in the art will recognize such feature, structure, or characteristic in connection with other embodiments whether or not explicitly described.

Implementations of the systems, apparatuses, devices, and methods disclosed herein may comprise or utilize one or more devices that include hardware, such as, for example, one or more processors and system memory, as discussed herein. An implementation of the devices, systems, and methods disclosed herein may communicate over a computer network. A "network" is defined as one or more data links that enable the transport of electronic data between computer systems and/or modules and/or other electronic devices. When information is transferred or provided over a network or another communications connection (either hardwired, wireless, or any combination of hardwired or wireless) to a computer, the computer properly views the connection as a transmission medium. Transmission media can include a network and/or data links, which can be used to carry desired program code means in the form of computer-executable instructions or data structures and which can be accessed by a general purpose or special purpose computer. Combinations of the above should also be included within the scope of non-transitory computer-readable media.

Computer-executable instructions comprise, for example, instructions and data which, when executed at a processor, cause the processor to perform a certain function or group of functions. The computer-executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

A memory device such as the memory 135 and the memory 148, can include any one memory element or a combination of volatile memory elements (e.g., random access memory (RAM, such as DRAM, SRAM, SDRAM, etc.)) and non-volatile memory elements (e.g., ROM, hard drive, tape, CDROM, etc.). Moreover, the memory device may incorporate electronic, magnetic, optical, and/or other types of storage media. In the context of this document, a "non-transitory computer-readable medium" can be, for example but not limited to, an electronic, magnetic, optical, electromagnetic, infrared, or semiconductor system, apparatus, or device. More specific examples (a non-exhaustive list) of the computer-readable medium would include the following: a portable computer diskette (magnetic), a random-access memory (RAM) (electronic), a read-only memory (ROM) (electronic), an erasable programmable read-only memory (EPROM, EEPROM, or Flash memory) (electronic), and a portable compact disc read-only memory (CD ROM) (optical). Note that the computer-readable medium could even be paper or another suitable medium upon which the program is printed, since the program can be electronically captured, for instance, via optical scanning of the paper or other medium, then compiled, interpreted or otherwise processed in a suitable manner if necessary, and then stored in a computer memory.

Those skilled in the art will appreciate that the present disclosure may be practiced in network computing environments with many types of computer system configurations, including in-dash vehicle computers, personal computers, desktop computers, laptop computers, message processors, handheld devices, multi-processor systems, microprocessor-based or programmable consumer electronics, network PCs, minicomputers, mainframe computers, mobile telephones, PDAs, tablets, pagers, routers, switches, various storage devices, and the like. The disclosure may also be practiced in distributed system environments where local and remote computer systems, which are linked (either by hardwired data links, wireless data links, or by any combination of hardwired and wireless data links) through a network, both perform tasks. In a distributed system environment, program modules may be located in both the local and remote memory storage devices.

Further, where appropriate, the functions described herein can be performed in one or more of hardware, software, firmware, digital components, or analog components. For example, one or more application specific integrated circuits (ASICs) can be programmed to carry out one or more of the systems and procedures described herein. Certain terms are used throughout the description, and claims refer to particular system components. As one skilled in the art will appreciate, components may be referred to by different names. This document does not intend to distinguish between components that differ in name, but not function.

It should be noted that the sensor embodiments discussed above may comprise computer hardware, software, firmware, or any combination thereof to perform at least a portion of their functions. For example, a sensor may include computer code configured to be executed in one or more processors and may include hardware logic/electrical circuitry controlled by the computer code. These example devices are provided herein for purposes of illustration and are not intended to be limiting. Embodiments of the present disclosure may be implemented in further types of devices, as would be known to persons skilled in the relevant art(s).

At least some embodiments of the present disclosure have been directed to computer program products comprising such logic (e.g., in the form of software) stored on any computer-usable medium. Such software, when executed in one or more data processing devices, causes a device to operate as described herein.

While various embodiments of the present disclosure have been described above, it should be understood that they have been presented by way of example only, and not limitation. It will be apparent to persons skilled in the relevant art that various changes in form and detail can be made therein without departing from the spirit and scope of the present disclosure. Thus, the breadth and scope of the present disclosure should not be limited by any of the above-described exemplary embodiments but should be defined only in accordance with the following claims and their equivalents. The foregoing description has been presented for the purposes of illustration and description. It is not intended to be exhaustive or to limit the present disclosure to the precise form disclosed. Many modifications and variations are possible in light of the above teaching. Further, it should be noted that any or all of the aforementioned alternate implementations may be used in any combination desired to form additional hybrid implementations of the present disclosure. For example, any of the functionality described with respect to a particular device or component may be performed by another device or component. Further, while specific device characteristics have been described, embodiments of the disclosure may relate to numerous other device characteristics. Further, although embodiments have been described in language specific to structural features and/or methodological acts, it is to be understood that the disclosure is not necessarily limited to the specific features or acts described. Rather, the specific features and acts are disclosed as illustrative forms of implementing the embodiments. Conditional language, such as, among others, "can," "could," "might," or "may," unless specifically stated otherwise, or otherwise understood within the context as used, is generally intended to convey that certain embodiments could include, while other embodiments may not include, certain features, elements, and/or steps. Thus, such conditional language is not generally intended to imply that features, elements, and/or steps are in any way required for one or more embodiments.

That which is claimed is:

1. A method comprising:
receiving, by a first computer in a vehicle, information regarding an occupant of the vehicle;
determining, by the first computer, based on the received information, a behavioral profile of the occupant of the vehicle;
determining, by the first computer, based on the behavioral profile, a behavior characteristic of the occupant of the vehicle;
matching, by the first computer, the behavior characteristic of the occupant to a first category in a set of behavior categories, wherein the set of behavior categories comprise an amaxophobia sufferer category, a controlling personality category, a complaining personality category, a passive personality category, a submissive personality category, and a judgmental personality category; and
executing, by the first computer, one or more operations in the vehicle based on matching the behavior characteristic of the occupant to the first category.

2. The method of claim 1, wherein the vehicle is an autonomous vehicle and wherein executing the one or more operations comprises at least one of displaying a video on an infotainment system in the autonomous vehicle or changing a driving characteristic of the autonomous vehicle.

3. The method of claim 1, wherein executing the one or more operations comprises offering the occupant of the vehicle a choice to modify a driving characteristic of the vehicle.

4. The method of claim 1, wherein executing the one or more operations comprises at least one of allowing the occupant to operate a user interface of a vehicle computer, modify a display of an infotainment system, or modify one or more settings of a climate control system.

5. The method of claim 1, wherein the vehicle is an autonomous vehicle and the method further comprises:
determining, by the first computer, based on data provided by one or more sensors in the vehicle, an anxiety level of the occupant of the vehicle; and
executing, by the first computer, one or more additional operations in the vehicle based on the anxiety level of the occupant of the vehicle.

6. A method comprising:
determining, by a first computer, based on data provided by one or more sensors in a vehicle, a behavior characteristic of an occupant of the vehicle, the behavior characteristic belonging to a first behavior category in a set of behavior categories, wherein the set of behavior categories comprise an amaxophobia sufferer category, a controlling personality category, a complaining personality category, a passive personality category, a submissive personality category, and a judgmental personality category; and
executing, by the first computer, one or more operations in the vehicle based on the behavior characteristic of the occupant of the vehicle.

7. The method of claim 6, wherein the vehicle is an autonomous vehicle and the first computer is located in the autonomous vehicle, and wherein the method further comprises:
receiving, by the first computer, from at least one of a second computer or a cloud storage component, information regarding the occupant of the vehicle;
determining, by the first computer, based on the information, a behavioral profile of the occupant of the vehicle;
determining, by the first computer, based on the behavioral profile and/or the behavior characteristic of the occupant, an anxiety level of the occupant of the vehicle; and
executing, by the first computer, the one or more operations in the vehicle based on the anxiety level of the occupant of the autonomous vehicle.

8. The method of claim 6, wherein the vehicle is an autonomous vehicle, the first computer is located in the autonomous vehicle, and the method further comprises:
offering the occupant of the vehicle a level of control upon one or more components in the vehicle.

9. The method of claim 6, wherein executing the one or more operations in the vehicle comprises displaying a video on an infotainment system and/or changing one or more driving characteristics of the vehicle.

10. The method of claim 6, further comprising:
modifying, by the first computer, a configuration of one or more seats of the vehicle based on determining an anxiety level of the occupant of the vehicle.

11. A first computer located in a vehicle, the first computer comprising:
at least one memory that stores computer-executable instructions; and
at least one processor configured to access the at least one memory and execute the computer-executable instructions to at least:
determine, based on data provided by one or more sensors in the vehicle, a behavior characteristic of an occupant of the vehicle, the behavior characteristic belonging to a first behavior category in a set of behavior categories, wherein the set of behavior categories comprise an amaxophobia sufferer category, a controlling personality category, a complaining personality category, a passive personality category, a submissive personality category, and a judgmental personality category; and
execute one or more operations in the vehicle based on the behavior characteristic of the occupant of the vehicle.

12. The first computer of claim 11, wherein the vehicle is an autonomous vehicle and the at least one processor is further configured to access the at least one memory and execute additional computer-executable instructions to at least:
receive, from at least one of a second computer or a cloud storage component, a behavioral profile of the occupant of the vehicle;
determine, based on the behavioral profile and/or the behavior characteristic of the occupant, an anxiety level of the occupant of the vehicle; and
execute the one or more operations in the vehicle based on the anxiety level of the occupant of the vehicle.

13. The first computer of claim 11, wherein the vehicle is an autonomous vehicle, and the at least one processor is further configured to access the at least one memory and execute additional computer-executable instructions to at least:
offer the occupant of the vehicle a level of control upon one or more components in the vehicle.

14. The first computer of claim 11, wherein the one or more operations comprises displaying a video on an infotainment system, or changing one or more driving characteristics of the vehicle.

15. The first computer of claim 11, wherein the vehicle is an autonomous vehicle, and the at least one processor is further configured to access the at least one memory and execute additional computer-executable instructions to at least:
modify a configuration of one or more components of the vehicle based on the behavior characteristic of the occupant of the vehicle.

16. The first computer of claim 15, wherein modifying the configuration of the one or more components of the vehicle comprises:
automatically rotating a front-facing seat in which the occupant is seated, to face a rear section of the vehicle.

17. The method of claim 1, wherein the vehicle is an autonomous vehicle and wherein executing the one or more operations in the autonomous vehicle comprises modifying a first set of operations of the autonomous vehicle when the occupant of the vehicle belongs to the amaxophobia sufferer category.

18. The method of claim 1, wherein executing the one or more operations in the vehicle comprises at least one of modifying a first set of operations of the vehicle when the occupant of the vehicle belongs to the amaxophobia sufferer category or modifying the first set of operations and/or a second set of operations of the vehicle when the occupant of the vehicle belongs to a controlling personality category.

19. The method of claim 6, wherein the vehicle is an autonomous vehicle and wherein the set of behavior categories includes the amaxophobia sufferer category.

* * * * *